US012551346B2

(12) United States Patent
Dees, Jr. et al.

(10) Patent No.: US 12,551,346 B2
(45) Date of Patent: Feb. 17, 2026

(54) TIBIAL IMPLANT WITH IMPROVED ANTERIOR LOAD TRANSFER

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Roger R. Dees, Jr., Drummonds, TN (US); Forrest A. James, Oakland, TN (US); Matthew J. Quick, Memphis, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 510 days.

(21) Appl. No.: 18/009,947

(22) PCT Filed: Jul. 21, 2021

(86) PCT No.: PCT/US2021/042465

§ 371 (c)(1),
(2) Date: Dec. 12, 2022

(87) PCT Pub. No.: WO2022/026256

PCT Pub. Date: Feb. 3, 2022

(65) Prior Publication Data

US 2023/0225867 A1 Jul. 20, 2023

Related U.S. Application Data

(60) Provisional application No. 63/058,928, filed on Jul. 30, 2020.

(51) Int. Cl.
*A61F 2/38* (2006.01)
*A61F 2/30* (2006.01)

(52) U.S. Cl.
CPC ...... *A61F 2/30* (2013.01); *A61F 2002/30878* (2013.01); *A61F 2002/30884* (2013.01); *A61F 2002/3092* (2013.01); *A61F 2/389* (2013.01)

(58) Field of Classification Search
None
See application file for complete search history.

(56) References Cited

U.S. PATENT DOCUMENTS 5,480,445 A 1/1996 Burkinshaw
9,381,085 B2 7/2016 Axelson, Jr.
(Continued)

OTHER PUBLICATIONS

International Search Report and Written Opinion for the International Patent Application No. PCT/US2021/042465, mailed Oct. 26, 2021, 14 pages.
(Continued)

*Primary Examiner* — Megan Y Wolf
(74) *Attorney, Agent, or Firm* — KDW Firm PLLC

(57) ABSTRACT

A knee prosthesis (e.g., a tibial implant or component) is disclosed. In one embodiment, the tibial implant includes a load bearing component (e.g., a tibial tray) and a support member arranged and configured to be at least partially positioned within an intramedullary canal of a patient's bone. In some embodiments, the tibial implant may also include one or more pegs positioned anteriorly on a bottom surface of the tray and one or more bridges for coupling the pegs to the support member so that loads received by the pegs are transferred to the support member via the bridge. In addition, and/or alternatively, the tibial implant may include one or more chamfers or loading zones for elongating the transition area between the support member and the bottom surface of the tibial tray to extend the area over which the load is transferred.

19 Claims, 13 Drawing Sheets

(56) References Cited

U.S. PATENT DOCUMENTS

| | | | | |
|---|---|---|---|---|
| 2008/0114462 | A1 | 5/2008 | Guidera | |
| 2012/0041564 | A1* | 2/2012 | Landon | A61F 2/30767 623/20.34 |
| 2014/0257507 | A1 | 9/2014 | Wang | |
| 2016/0278929 | A1 | 9/2016 | Harris | |
| 2018/0333267 | A1 | 11/2018 | Landon | |
| 2019/0151102 | A1 | 5/2019 | Hagen | |
| 2019/0343639 | A1 | 11/2019 | Nguyen | |
| 2020/0306050 | A1 | 10/2020 | Harmon | |

OTHER PUBLICATIONS

No author or publisher—Bottom Surface of a tibial base plate—May 2020.

* cited by examiner

TIBIAL IMPLANT WITH IMPROVED ANTERIOR LOAD TRANSFER

CROSS-REFERENCE TO RELATED APPLICATIONS

This application is a National Phase filing of International Application No. PCT/US2021/042465, filed Jul. 21, 2021, which is a non-provisional of, and claims the benefit of the filing date of, U.S. provisional patent application No. 63/058,928, filed Jul. 30, 2020, entitled "Tibial Implant with Improved Anterior Load Transfer," the entirety of each application is incorporated by reference herein.

FIELD OF THE DISCLOSURE

The present disclosure is directed to an orthopedic implant, and more particularly to an orthopedic knee prosthesis for a proximal tibia such as, for example, an improved tibial implant for handling anterior loading.

BACKGROUND

Knee arthroplasty or knee replacement procedures generally involve the implantation, installation, etc. (used interchangeably herein without the intent to limit) of an orthopedic implant such as a knee prosthesis onto a patient's knee. For example, in connection with a total knee replacement, the orthopedic implant (e.g., knee prosthesis) may include a femoral implant and a tibial implant. In use, the femoral implant is attached to the patient's femur while the tibial implant is attached to the patient's tibia. Generally speaking, the femoral and tibial implants may each include a support member (e.g., an intramedullary stem), which is attachable to an articular component, a tray, a load bearing component, etc. (terms used interchangeably herein without the intent to limit). In use, the support member is arranged and configured to be inserted within an intramedullary canal of the patient's bone while the tray mounts upon a prepared surface on the patient's bone. A bearing member or insert is typically mounted upon the tray of the tibial implant.

There are several factors that are potentially relevant to the design and performance of orthopedic implants. For example, in connection with an orthopedic tibial implant, a non-exhaustive list of such factors includes the implant's flexibility (or the flexibility of certain portions of the implant or its flexibility about certain axes or other constructs), which may indicate the degree to which the tray conforms to the potentially uneven resected surfaces of a proximal tibia; the implant's rigidity (or the rigidity of certain portions of the implant or its rigidity about certain axes or other constructs), which may indicate the degree to which stresses or other forces imposed by the bone and other anatomy associated with the knee joint are transmitted to the peripheral hard cortical shell of the proximal tibia; the implant's resistance to rotation; the amount of bone preserved; and/or other potentially relevant factors. In some instances, accommodation of these or other factors may require tradeoffs to balance competing factors. In some instances, one or more of these factors may not be considered or given a high level of importance to the design of an orthopedic implant.

One known knee prosthesis is Journey II manufactured and distributed by Smith Nephew, Inc. In use, the Journey II knee prosthesis attempts to substantially mimic the kinematics of the patient's natural knee. Specifically, for example, the Journey II knee prosthesis includes a convex lateral side that substantially mimics the convex lateral side of a natural tibia. As a result, the patient's femur is permitted to lock forward in a screw home position, which mimics the screw home position of the natural knee. One consequence of mimicking the natural screw home position is that the tibial implant of the knee prosthesis experiences loading anteriorly on the tibial tray.

It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one embodiment, a knee prosthesis (e.g., a tibial implant or component) is disclosed. The tibial implant comprises a tibial tray and a support member, the tibial tray including a top surface and a bottom surface, the support member extending from the bottom surface of the tibial tray, the support member being arranged and configured to be at least partially positioned within an intramedullary canal of a patient's bone for coupling the tibial implant to the patient's bone during use. The support member including a stem portion, one or more keels extending from the stem portion, one or more pegs positioned anteriorly on the bottom surface of the tibial tray, and one or more bridge members coupling the one or more pegs to the one or more keels, respectively, the one or more bridge members arranged and configured to transfer loads from the one or more pegs to the one or more keels.

In one embodiment, the tibial implant comprises a tibial tray including a top surface and a bottom surface and a support member extending from the bottom surface of the tibial tray. The support member is arranged and configured to be at least partially positioned within an intramedullary canal of a patient's bone for coupling the tibial implant to the patient's bone during use. The support member includes a stem portion and one or more keels extending from the stem portion. The tibial implant further comprises a chamfer loading zone between the bottom surface of the tibial tray and the support member, the chamfer loading zone providing a variable thickness transition area between the bottom surface of the tibial tray and the support member to transfer loads between the tibial tray and the support member.

In one embodiment, the one or more keels includes first and second keels, the one or more pegs include first and second pegs, and the one or more bridge members include first and second bridge members, the first peg being coupled to the first keel via the first bridge member, the second peg being coupled to the second keel via the second bridge member.

In one embodiment, the first keel extends from the medial side of the stem portion toward the medial side of the tibial tray, the second keel extends from the lateral side of the stem portion toward the lateral side of the tibial tray.

In one embodiment, the first and second keels extend posteriorly from the stem portion.

In one embodiment, the first and second pegs are positioned closer to a periphery edge of the tibial tray as compared to the stem portion.

In one embodiment, the first and second pegs are positioned anteriorly as compared to the stem portion.

In one embodiment, the tibial tray and the support member including the stem portion, the one or more keels, the one or more pegs, and the one or more bridge members are monolithically or integrally formed.

In one embodiment, the bottom surface of the tibial tray further comprises a porous layer mounted thereon.

In one embodiment, the support member includes one or more protrusions coupled to the stem portion, the one or more protrusions extending along a longitudinal length of the stem portion.

In one embodiment, the support member includes one or more protrusions coupled to the one or more keels, the one or more protrusions extending along a longitudinal length of the keels.

In one embodiment, the tibial implant further comprises a chamfer loading zone between the bottom surface of the tibial tray and the support member, the chamfer loading zone providing a variable thickness transition area between the bottom surface of the tibial tray and the support member to transfer loads between the tibial tray and the support member.

In one embodiment, the chamfer loading zone is positioned between a radiused surface associated with the support member and the bottom surface of the tibial tray.

In one embodiment, each of the stem portion, the one or more keels, the one or more pegs, and the one or more bridge members includes a chamfer loading zone extending therefrom.

In one embodiment, the chamfer loading zone is arranged and configured to provide the tibial tray with a variable thickness to transition the bottom surface of the tibial tray to the support member while an overall combined thickness of the tibial tray and a porous coating applied thereon remains constant.

In one embodiment, each of the chamfer loading zones includes a circular shape extending outwardly from the support member.

In an alternate embodiment, a tibial implant is disclosed. The tibial implant comprising a tibial tray and a support member, the tibial tray including a top surface and a bottom surface, the support member extending from the bottom surface, the support member being arranged and configured to be at least partially positioned within an intramedullary canal of a patient's bone for coupling the implant to the patient's bone during use. The tibial implant further comprising a chamfer loading zone between the bottom surface of the tibial tray and the support member, the chamfer loading zone providing a variable thickness transition area between the bottom surface of the tibial tray and the support member to guide distribution of a load between the tibial tray and the support member.

In one embodiment, the chamfer loading zone is positioned between a radiused surface associated with the support member and the bottom surface of the tibial tray.

In one embodiment, the support member includes a stem portion, one or more keels extending from the stem portion, and one or more pegs positioned anteriorly on the bottom surface of the tibial tray, each of the stem portion, the one or more keels, and the one or more pegs, includes a chamfer loading zone extending therefrom.

In one embodiment, each of the chamfer loading zones includes a circular shape extending outwardly from the stem portion, the one or more keels, and the one or more pegs.

In one embodiment, the chamfer loading zone is arranged and configured to provide the tibial tray with a variable thickness to transition the bottom surface of the tibial tray to the support member while an overall combined thickness of the tibial tray and a porous coating applied thereon remain constant.

In one embodiment, the one or more pegs are coupled to the one or more keels, respectively, via one or more bridge members, respectively, so that anterior loading on the pegs is transferred to the keels via the bridge members.

In one embodiment, at least a portion of the porous layer comprises a non-faceted bottom surface arranged and configured to provide a variable thickness transition area between the bottom surface of the tibial tray and the support member to guide distribution of a load between the tibial tray and the support member.

In an alternate embodiment, a tibial implant is disclosed. The tibial implant comprising a tibial tray and a support member, the tibial tray including a top surface and a bottom surface, the support member extending from the bottom surface, the support member being arranged and configured to be at least partially positioned within an intramedullary canal of a patient's bone for coupling the tibial implant to the patient's bone during use. The tibial tray further comprising a porous surface including a non-faceted bottom surface. In one embodiment, the non-faceted bottom surface of the porous surface conceals chamfer loading zones arranged and configured to provide a variable thickness transition area between the bottom surface of the tibial tray and the support member to guide distribution of a load between the tibial tray and the support member.

In one embodiment, the non-faceted porous structure nests into a precision prepared proximal tibia. The proximal tibia is prepared with precision milling via, for example, a bur. Strategic chamfer zones and added material may be embedded within the non-faceted porous structure to provide optimal support for in vivo loading.

Embodiments of the present disclosure provide numerous advantages. For example, by providing bridge members between the pegs and the keels, the tibial implant is better able to handle and distribute loads experience by an anterior portion of the tibial tray. Similarly, by incorporating chamfer loading zones between the tibial tray and the support member, the tibial implant is better able to distribute loads experienced during use while minimizing the overall thickness of the tibial tray.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
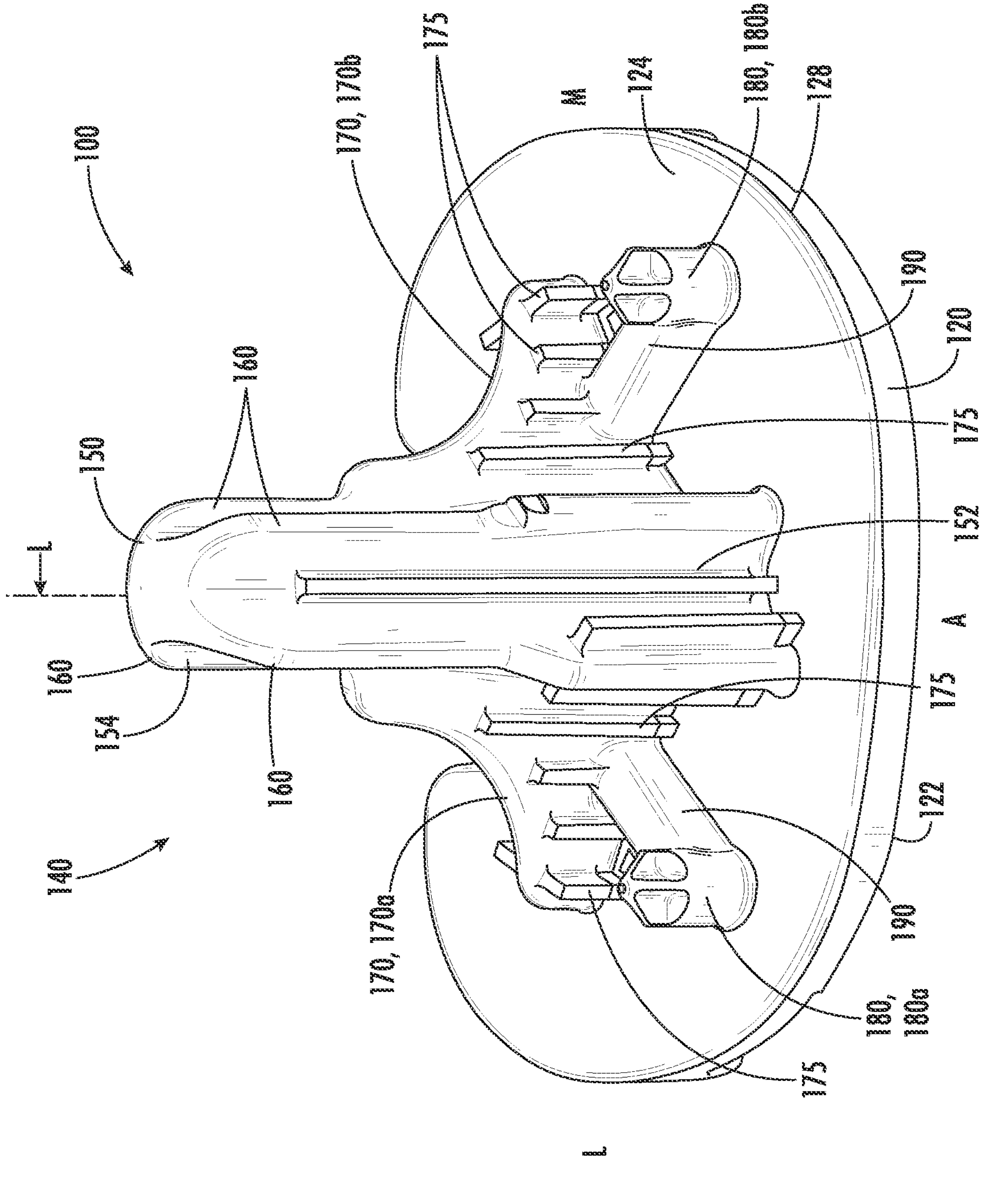
FIG. 1 is a bottom, perspective view of an example of an embodiment of an orthopedic tibial implant in accordance with one or more features of the present disclosure.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

DETAILED DESCRIPTION

Various features or the like of an orthopedic implant such as a knee prosthesis (e.g., a tibial implant or component) will now be described more fully hereinafter with reference to the accompanying drawings, in which one or more features of the knee prosthesis will be shown and described. It should be appreciated that the various features or the like may be used independently of, or in combination, with each other. It will be appreciated that a knee prosthesis as disclosed herein may be embodied in many different forms and should not be construed as being limited to the embodiments set forth herein. Rather, these embodiments are provided so that this disclosure will convey certain features of the knee prosthesis to those skilled in the art. In the drawings, like numbers refer to like elements throughout unless otherwise noted.

As will be described herein, in accordance with one or more features of the present disclosure, a knee prosthesis such as a tibial implant, component, etc. (used interchangeably herein without the intent to limit) is disclosed. In one embodiment, the knee prosthesis includes a tibial tray or load bearing component (terms used interchangeably herein without the intent to limit) and a support member including an intramedullary stem arranged and configured for implantation into an intramedullary canal of a patient's bone such as, for example, the patient's tibia. In addition, in accordance with one feature of the present disclosure, the tibial tray further includes one or more pegs positioned anteriorly on a bottom surface of the tray and one or more bridges for coupling the pegs to the support member so that loads received by the pegs are transferred to the support member. In addition, in accordance with another feature of the present disclosure that may be used in combination or separately from the other features of the present disclosure disclosed herein, the tibial implant may include one or more chamfers or loading zones for elongating the transition area between the support member and the bottom surface of the tibial tray to extend the area over which the load is transferred.

Figure 2:
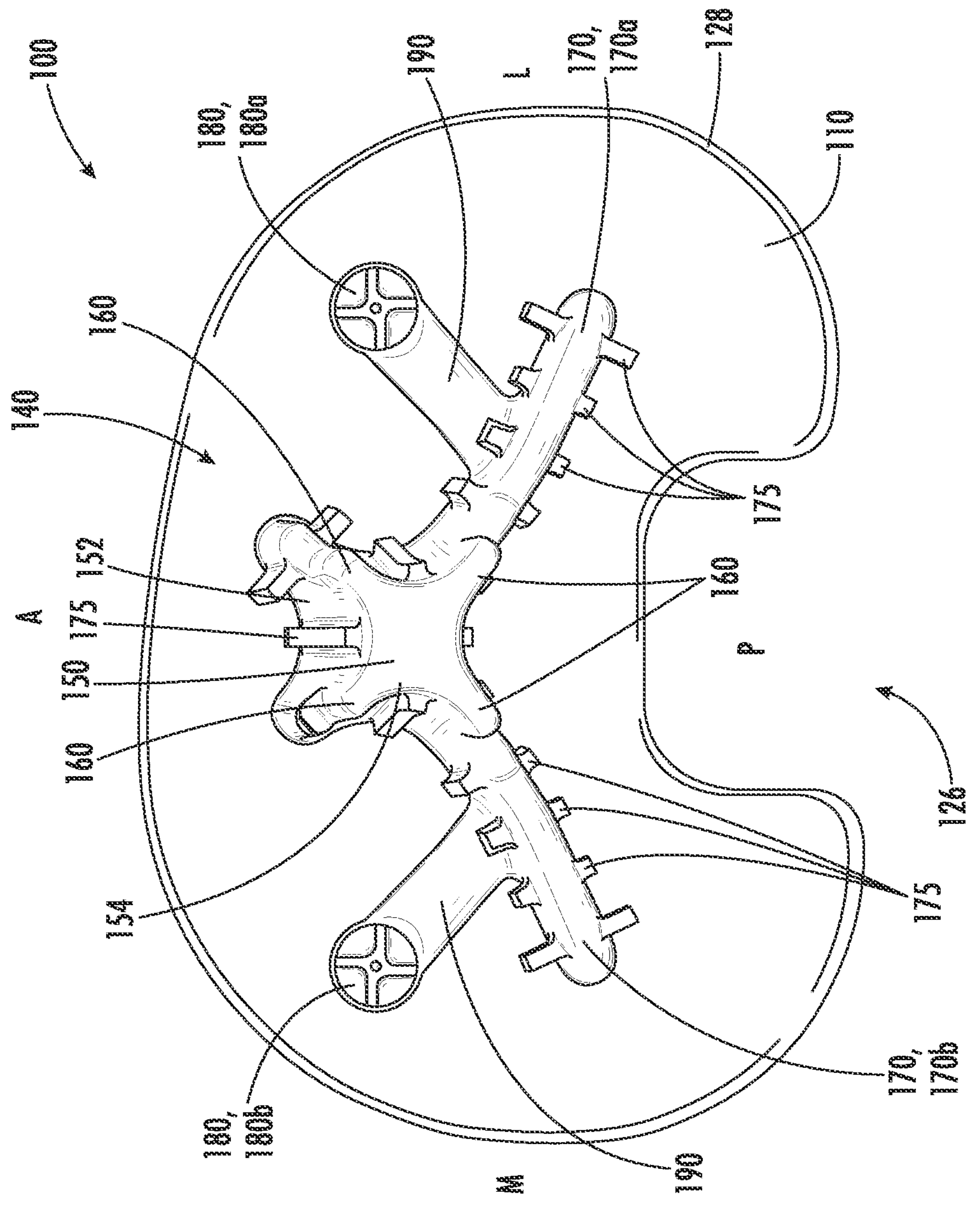
FIG. 2 is a bottom view of the tibial implant shown in FIG. 1.
Figure 3:
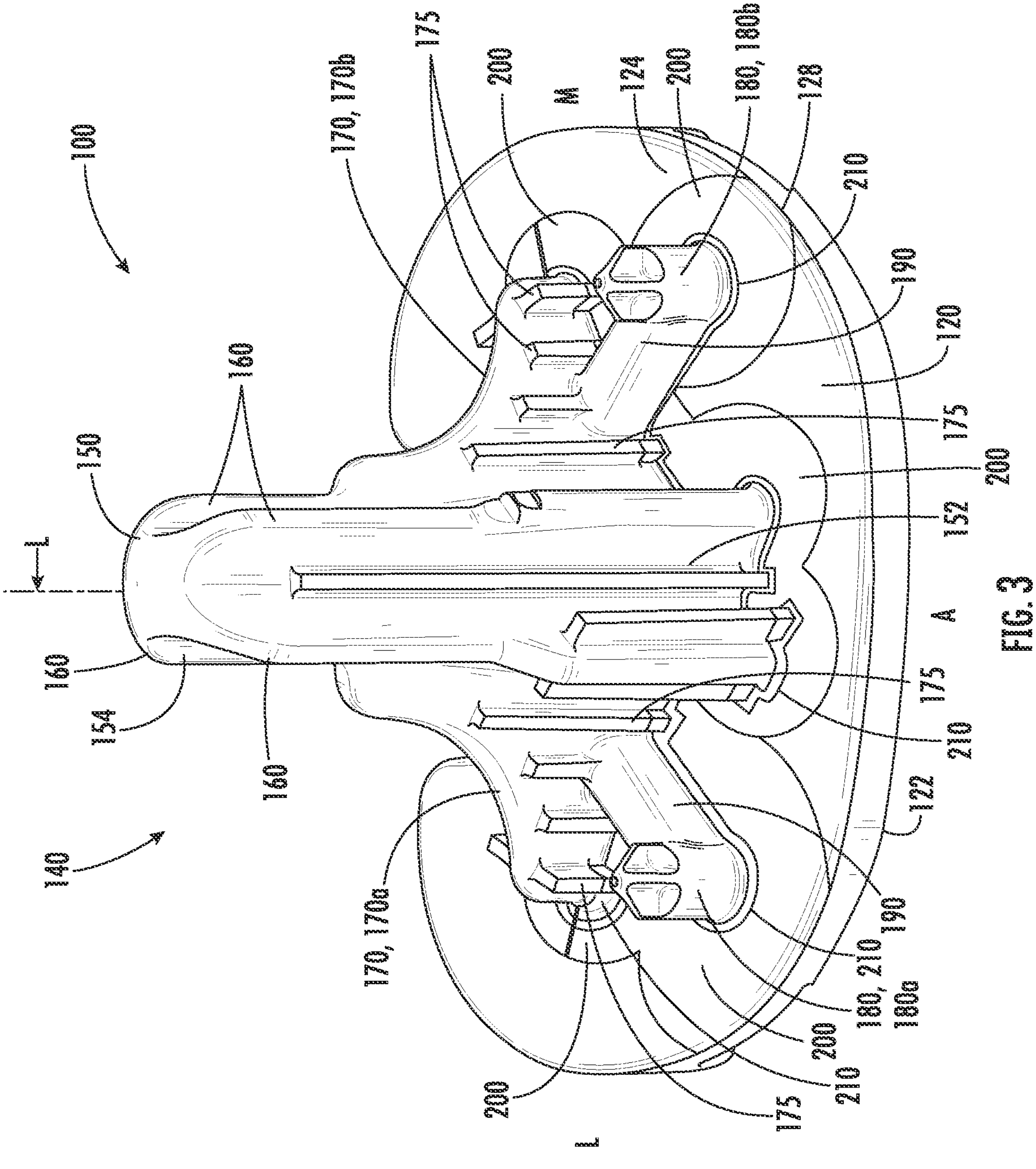
FIG. 3 is a bottom, perspective view of the tibial implant shown in FIG. 1, the tibial implant shown with the porous layer removed.
Figure 4:
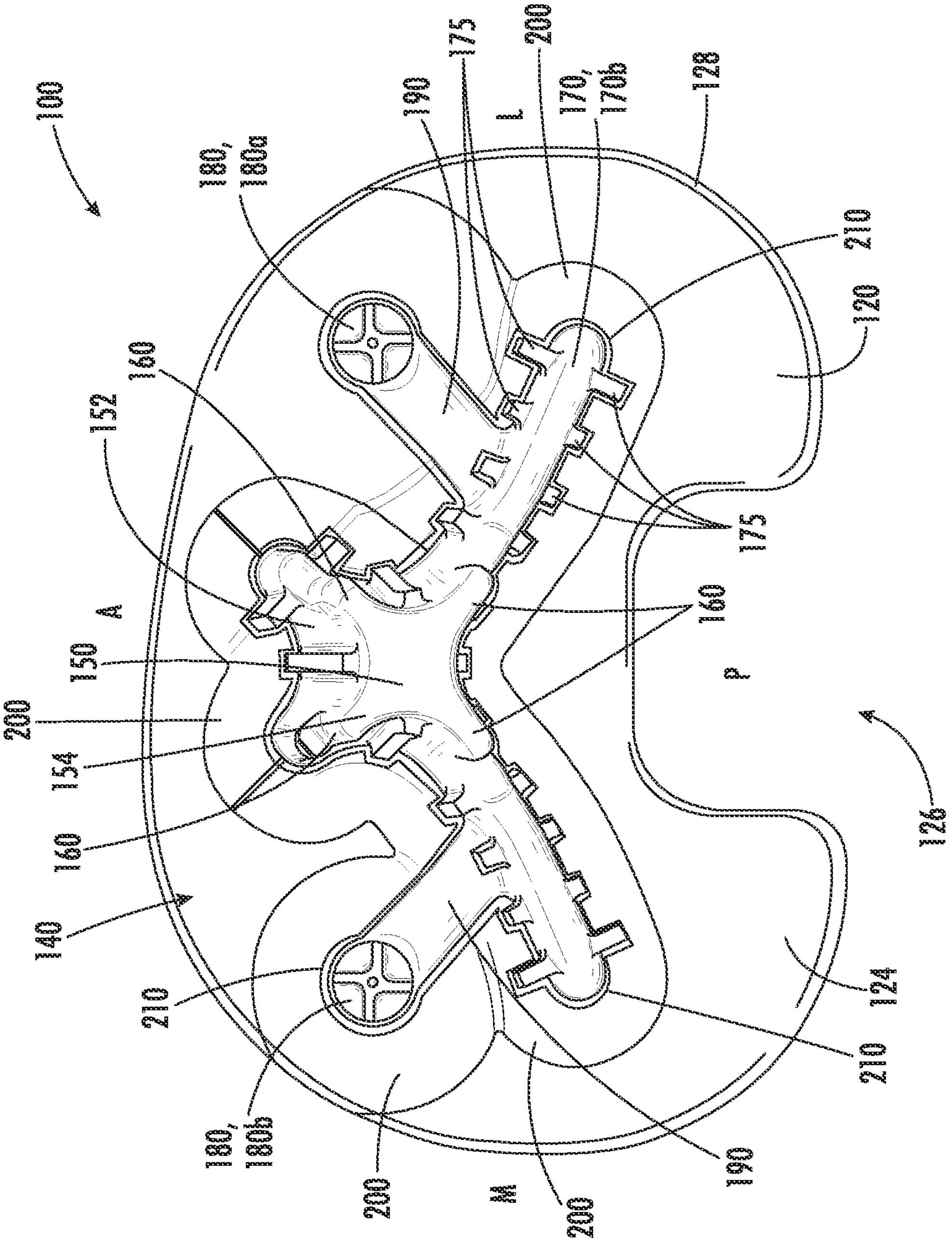
FIG. 4 is a bottom view of the tibial implant shown in FIG. 1, the tibial implant shown with the porous layer removed.

Referring to FIGS. 1-4, an example of an embodiment of a tibial implant 100 is illustrated. FIGS. 1 and 2 illustrate a bottom view of the tibial implant 100 with a porous layer 110 coupled thereto or mounted thereon. FIGS. 3 and 4 illustrate a bottom view of the tibial implant 100 with the porous layer 110 removed.

As shown, the tibial implant 100 includes a tibial tray 120 connected to a support member 140. The support member 140 can be connected to the tibial tray 120 by any technique now known or hereafter developed including, for example, a threaded connection, a press-fit, an adhesive, cement, or other techniques. In one embodiment, the support member 140 is monolithic or integrally formed with the tibial tray 120. For example, in one embodiment, the tibial tray 120 and the support member 140 may be monolithically or integrally formed using any now known or hereafter developed technique or method including, for example, additive manufacturing techniques. For example, some non-limiting additive manufacturing techniques include selective laser sintering (SLS), direct metal laser sintering (DMLS), electron beam melting (EBM), selective laser melting (SLM), three-dimensional printing, or the like.

As illustrated, the tibial tray includes a top or superior surface 122 and a bottom or inferior surface 124. As illustrated in FIGS. 1 and 2, the bottom surface 124 of the tibial tray 120 includes a porous layer or coating 110 applied thereto. For example, in one embodiment, the porous coating or layer 110 is a titanium layer that may be applied to the bottom surface 124 of the tibial tray 120. The porous coating or layer 110 may be applied to the bottom surface 124 of the tibial tray 120 by any now known or hereafter developed technique or method. For example, the porous coating or layer 110 may be applied to the bottom surface 124 of the tibial tray 120 via an additive manufacturing technique. For example, some non-limiting additive manufacturing techniques include selective laser sintering (SLS), direct metal laser sintering (DMLS), electron beam melting (EBM), selective laser melting (SLM), three-dimensional printing, or the like.

In use, the top surface 122 of the tibial tray 120 may include a lip or lock (not shown) for receiving and/or securing one or more inserts (not shown) to the tibial tray 120, such inserts may be designed to contact and articulate with a femoral orthopedic implant (not shown) in use. Alternatively, the tibial tray 120 itself may include articular surfaces that do not require separate articular inserts. In one embodiment, as shown, the tibial tray 120 may include a posterior notch 126, which may be designed to allow preservation of the attachment site of a posterior cruciate ligament, although, in other embodiments, the tibial tray 120 may or may not include this or other notches or gaps for preserving one or both of the cruciate ligaments. In other words, the tibial tray 120, in some embodiments, may be for use in a cruciate sacrificing procedure, a posterior cruciate preserving procedure, or a bi-cruciate preserving procedure. In some embodiments, the tibial tray 120 may be used for a mobile bearing knee joint or a fixed bearing knee joint. It will be appreciated that a variety of top surfaces and peripheral shapes are possible according to various embodiments and that such shapes can be influenced, at least in part, by strength requirements for the tray 120.

As shown, the support member 140 extends from the bottom surface 124 of the tibial tray 120. In use, the support member 140 is positioned, at least partially, within the intramedullary canal of the patient's tibia to couple the tibial implant 100 to the patient's tibia. In one embodiment, as shown, the support member 140 includes a stem portion 150 that extends away from the bottom surface 124 of the tibial tray 120 along a longitudinal axis L. In the illustrated embodiment, the longitudinal axis L is substantially perpendicular to the bottom surface 124 of the tibial tray 120 in the medial-lateral direction, but other angles may be used. Additionally, in some embodiments, the tibial tray 120 may include a slope in the anterior-posterior direction. For example, the tibial tray 120 can have a 3 to 7 degree posterior slope. Alternatively, the tibial tray 120 can have a zero degree slope. The stem portion 150 may be positioned offset from a center of the tibial tray 120 (e.g., positioned more medial than lateral). For example, in one embodiment, the stem portion 150 may be medialized slightly from the center of the tibial tray 120. For example, the stem portion 150 can be medialized 1 to 3 mm from the center of the tibial tray 120. In other embodiments, the stem portion 150 may be centered on the tibial tray 120.

In some embodiments, the stem portion 150 may include a first portion 152 adjacent to the bottom surface 124 of the tibial tray 120 and a second portion 154 that extends away from the first portion 152. The first portion 152 may have a first cross sectional area and the second portion 154 may have a second cross sectional area wherein the first cross sectional area is larger than the second cross sectional area. In other embodiments, the second portion 154 can have the same cross sectional area and shape as the first portion 152. In use, the stem portion 150 has a length that is sized to promote varus-valgus stability and resistance of the tibial tray 120 to liftoff from the patient's bone.

In one embodiment, as shown, the support member 140 may include one or more fins 160 spaced about the stem portion 150. For example, as illustrated, the stem portion 150 may include four fins 160 spaced thereabout, although this is but one configuration and more or less fins 160 may be used. Moreover, in one embodiment, the fins 160 can be spaced equally from each other or in another arrangement as desired. In one embodiment, the fins 160 may extend along the support member 140 towards the second portion 154 in a tapering configuration. In use, the fins 160 assist in providing rotational stability and help with implantation and alignment of the tibial tray 120 in bone upon implantation. Any or all of the fins 160 can also be sized to a maximum that is implantable based on the anatomy of the patient.

In addition, as shown, the support member 140 may also include one or more posterior keels or arms 170 (terms used interchangeably herein without the intent to limit). As shown, the support member 140 may include first and second posterior keels 170*a*, 170*b* mounted on the bottom surface 124 of the tibial tray 120 extending from either side of the stem portion 150 posteriorly towards the posterior side P of the tibial tray 120, although this is just one configuration and more or less keels 170 and/or different configurations of keels 170 may be utilized. In use, the keels 170 may increase the strength of the implant 100 while also helping to prevent rotation of the tibial implant 100 relative to the patient's bone (e.g., keels 170 assist with rotational stability of the tibial tray 120 in bone upon implantation).

As illustrated, in one embodiment, the first keel 170*a* may be angled relative to the second keel 170*b*, but in other embodiments the first and second keels 170*a*, 170*b* may be substantially aligned with one another. In one embodiment, the first and second keels 170*a*, 170*b* may be separated from each other via an angle ranging from about 10 degrees to about 180 degrees. As illustrated, in one embodiment, the first and second keels 170*a*, 170*b* may have a similar shape and size, however, in other embodiments, the first and second keels 170*a*, 170*b* may be provided with different shapes and sizes. In one embodiment, the first and second keels 170*a*, 170*b* curve or curl towards the medial M and lateral L sides, respectively, of the tray 120.

The first and second keels 170*a*, 170*b* extend longitudinally along the support member 140 towards the second portion 154; however, as illustrated, the first and second keels 170*a*, 170*b* may be shorter or smaller than the fins 160 and, as such, do not extend as far longitudinally as the fins 160 along the support member 140. Each of the first and second keels 170*a*, 170*b* may have a horizontal length that extends towards a rim or periphery edge 128 of the tibial tray 120. The first and second keels 170*a*, 170*b* may each have a sharp edge.

As illustrated, the first and second keels 170*a*, 170*b*, as well as other components of the support member 140, may include a plurality of rail protrusions or ridges 175 (terms used interchangeably herein without the intent to limit) that extend along the height or a portion of the keels 170 as measured along the longitudinal axis L. In one embodiment, the plurality of ridges 175 may have a square or semi square cross sectional shape however in other forms the shape may be rectangular or semicircular. The plurality of ridges 175 can have a variable height and a variable width such that one or more of the plurality of ridges 175 has a unique height and width. For example, in some forms, the height and width of the plurality of ridges 175 can range between 1 and 3 millimeters. The plurality of ridges 175 can be spaced along the keels 170 in a uniform spacing arrangement or non-uniform spacing arrangement. The plurality of ridges 175 assist with added bone compression and fixation strength of the tibial implant 100 in the patient's bone.

Beneficially, the fins 160 and the keels 170 provide increased rotational resistance and strength for the tibial implant 100 when implanted. The configuration of the support member 140 including the stem portion 150, fins, 160, and keels 170 provide improved fixation between the tibial tray 120 and the patient's bone post-operatively. Moreover, the fins 160 positioned on the anterior side A of the tibial tray 120 are more sensitive to anatomic dimensions of the patient's bone than the fins 160 positioned on the posterior side P therefore the size, location, and position of the anterior fins 160 on the tibial tray 1120 are more sensitive than the posterior fins 160.

In addition, as illustrated, in one example of an embodiment, the tibial tray 120 may also include one or more pegs 180. For example, as shown, the tibial implant 100 may include first and second pegs 180*a*, 180*b*, although this is but one configuration and more or less pegs may be used. As illustrated, the first and second pegs 180*a*, 180*b* may be mounted on the bottom surface 124 of the tibial tray 120. The pegs 180 can be connected to the tibial tray 120 by any technique now known or hereafter developed including, for example, threaded connection, press-fit, adhesive, cement, or other techniques. In one embodiment, the pegs 180 are monolithic or integrally formed with the tibial tray 120.

In one embodiment, as illustrated, the first and second pegs 180*a*, 180*b* are positioned near the rim or periphery edge 128 of the tibial tray 120. The first and second pegs 180*a*, 180*b* approach the tibial plateau for added stability of the tibial tray 120, and enter into denser bone than in the central canal upon implantation. Additional pegs 180 can be mounted as desired. The pegs 180 can have any suitable size and shape arranged and configured to engage the patient's bone to provide increased stability. For example, as shown, the pegs 180 may be substantially cylindrical with a pointed tip, although other shapes are envisioned such as, for example, an arrowhead shape.

In accordance with one or more features of the present disclosure, in use, the pegs 180 such as, for example, the first and second pegs 180*a*, 180*b* may be coupled to the support member 140 such as, for example, to the first and second keels 170*a*, 170*b*, respectively, via a support rib, bridge or bridge member, radius, material, or the like 190 (terms used interchangeably herein without the intent to limit). As illustrated, in one embodiment, during use, the bridge 190 is arranged and configured to couple the first and second pegs 180*a*, 180*b* to the first and second keels 170*a*, 170*b*, respectively, so that any loads received by the first and second pegs 180*a*, 180*b* can be transferred to the support member 140 via the first and second keels 170*a*, 170*b*. Thus arranged, any anterior load can be carried back from the pegs 180, which are positioned anteriorly on the tray 120 to capture the anterior loads, to the keels 170 and subsequently to the support member 140 thereby providing the tibial tray 120 with increased strength to avoid breakage due to an associated anterior loading condition. That is, in contrast with known implants, by coupling the pegs 180 to the support member 140 via, for example, the keels 170, the anterior load is transferred from the pegs 180 to the keels 170 and to the stem portion 150 of the support member 140 instead of to the tray 120 thereby providing increased strength to avoid damage such as breakage of the tray.

In use, the bridge 190 may have any configuration now known or hereafter developed arranged and configured to transfer the load from the pegs 180 to the keels 170 to the stem portion 150 of the support member 140. That is, the bridge 190 may have any configuration arranged to protect the anterior loading area and to carry the stress back to the support member 140. For example, as shown, the bridge 190 may be manufactured from wrought material and be monolithically or integrally formed with the tray 120 and/or support member 140. Alternatively, it is envisioned that the bridges may include, for example, an open space (e.g., window), which could be filled with a lattice and/or porous structure. Alternatively, the bridges may incorporate a reduced cross sectional area, or be connected with struts.

While the pegs 180 and the bridges 190 have been shown and illustrated with a particular tibial tray and support member, it should be understood that the present disclosure is not so limited and that the pegs 180 and bridges 190 may be used with any tibial implant now known or hereafter developed unless specifically claimed.

Figure 8:
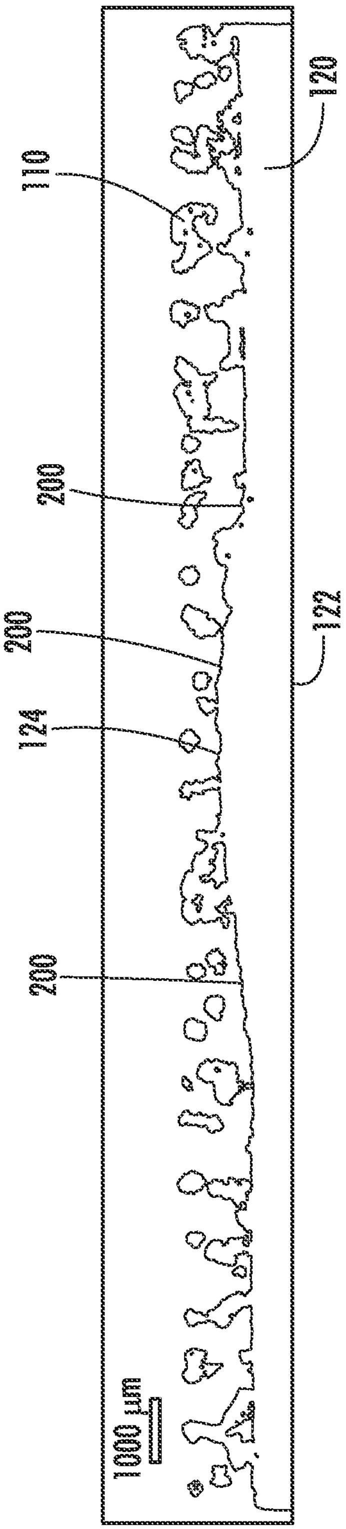
FIG. 8 illustrates a cross-sectional view illustrating the change in thickness created in a tibial tray by incorporating one or more chamfers or loading zones in accordance with one or more features of the present disclosure.
Figure 9:
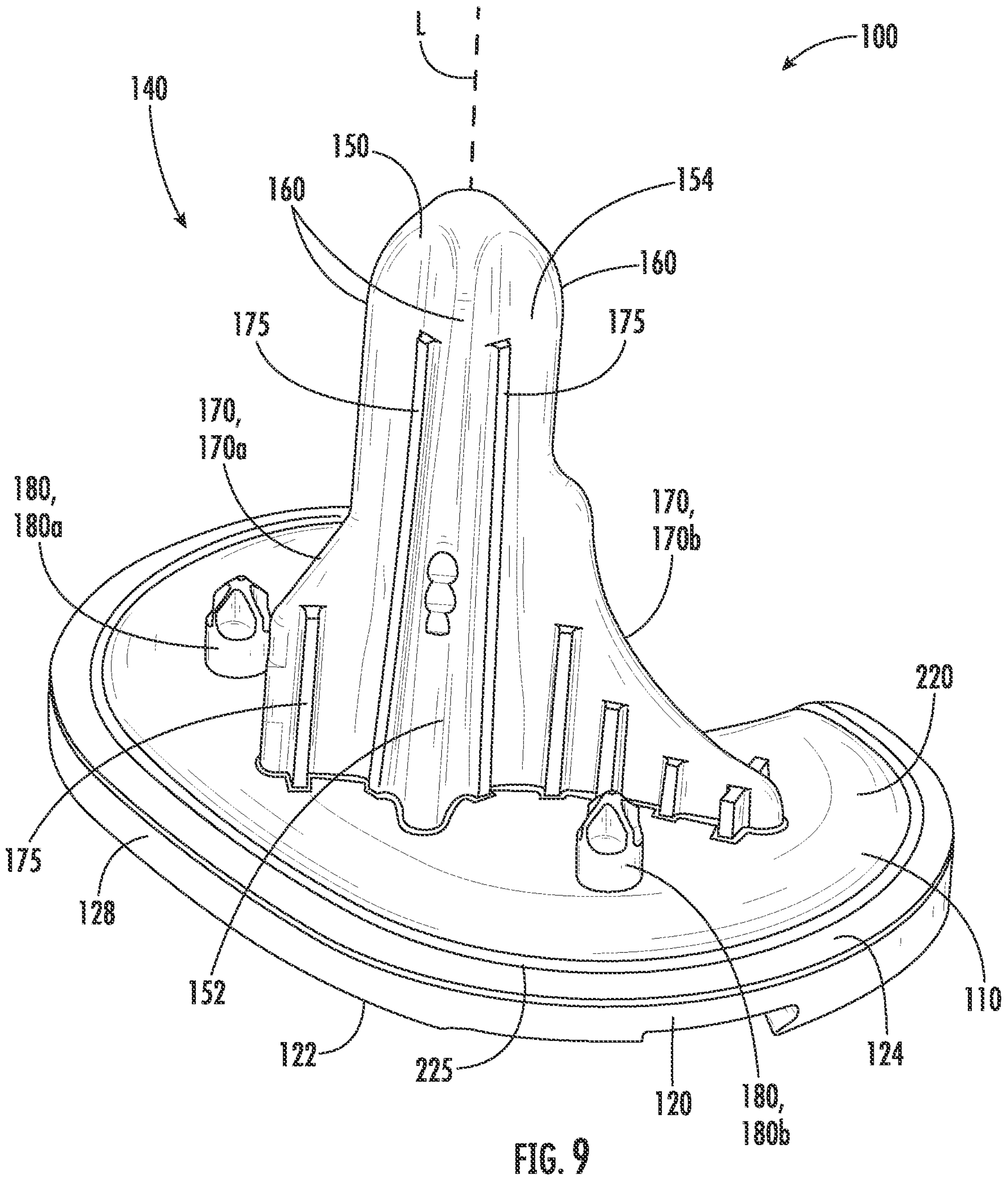
FIG. 9 illustrates a bottom, perspective view of an alternate example of an embodiment of a tibial implant in accordance with one or more features of the present disclosure, the tibial implant including a non-faceted porous bottom surface.
Figure 10:
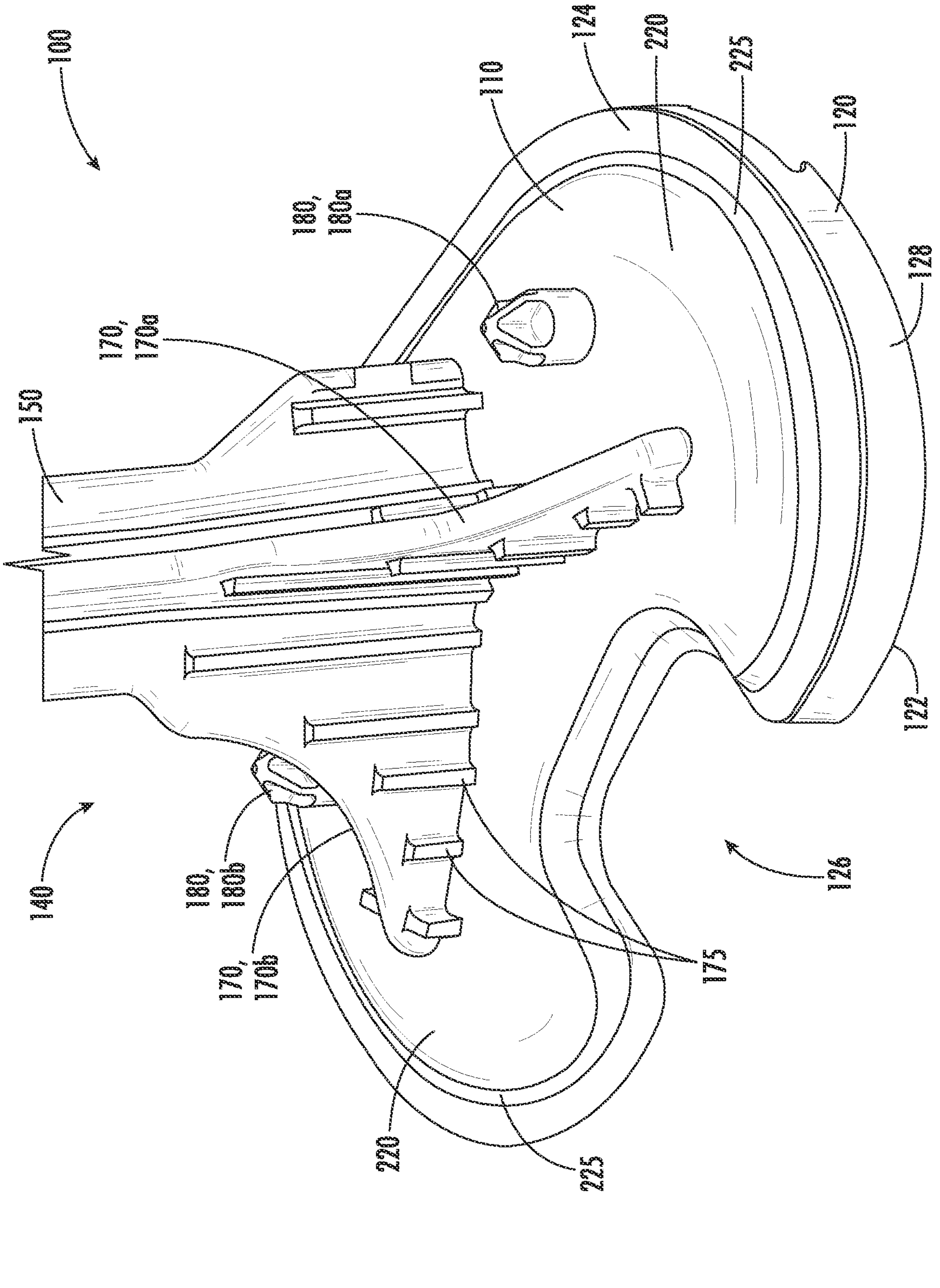
FIGS. 10-12 illustrate various alternate views of the tibial implant shown in FIG. 9.
Figure 11:
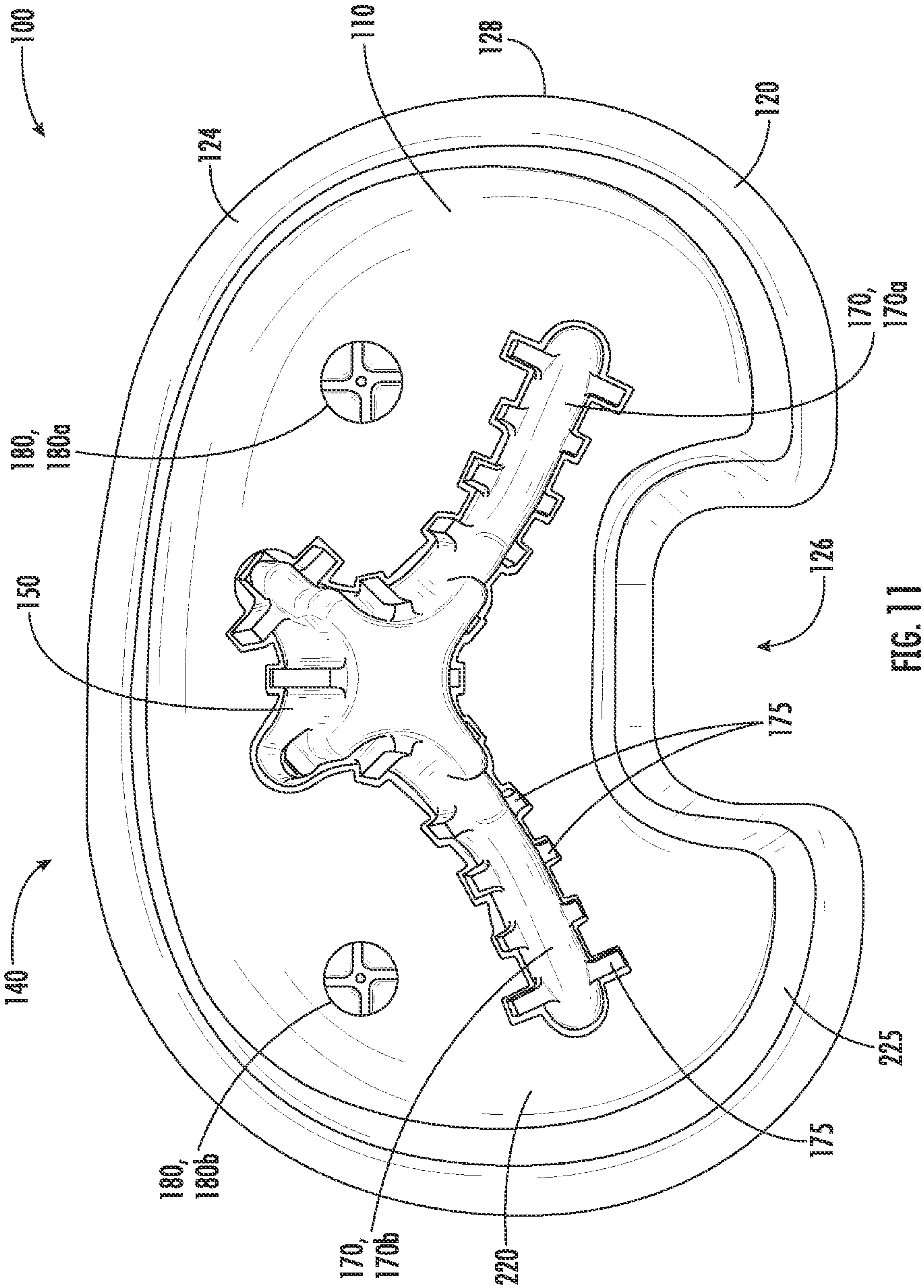
Figure 12:
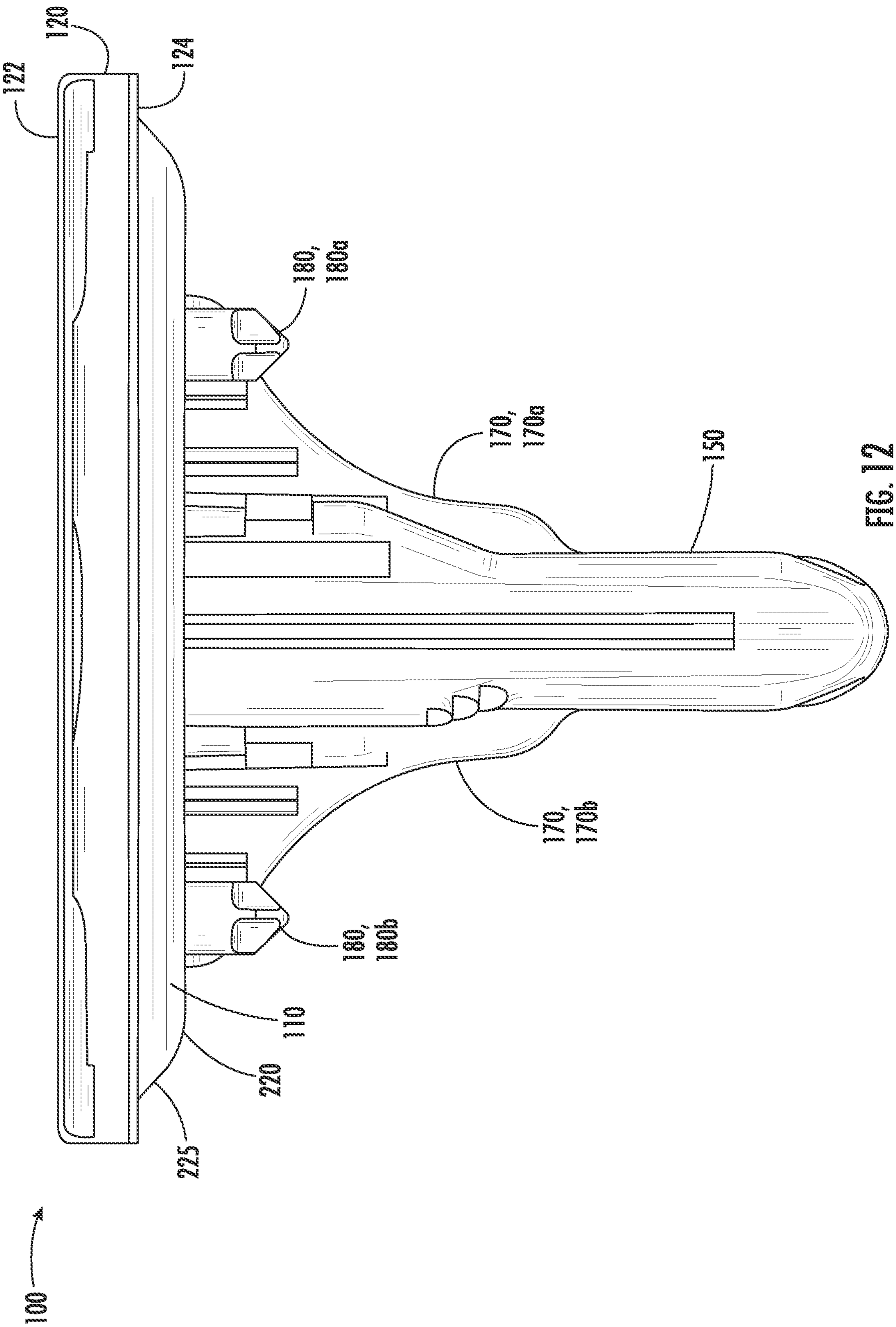

Referring to FIGS. 3 and 4, in accordance with one or more features of the present disclosure that may be used in combination with the pegs 180 and bridges 190 disclosed above or separately therefrom, the tibial tray 120 may include one or more chamfers 200 formed in the bottom or inferior surface 124 thereof. In addition, as illustrated in FIGS. 3 and 4, the support member 140 including the stem portion 150, keels 170, pegs 180, and bridges 190 may include a radiused surface 210 at the connection or formation to the bottom surface 124 of the tibial tray 120. In use, the radiused surface 210 facilitates transferring load between the support member 140 including the stem portion 150, keels 170, pegs 180, and bridges 190 and the tray 120 by preventing, or at least minimizing stress concentrations (e.g., the radiused surfaces 210 help to facilitate better load transfer back towards the support member). As illustrated, and in connection with one or more features of the present disclosure, the bottom surface 124 of the tray 120 may also include one or more chamfers 200 formed between the radiused surface 210 and the bottom surface 124 of the tibial tray 120. Referring to FIG. 8, which illustrates an example of an embodiment of a cross-sectional area of a tray 120 utilizing one or more chamfers 200, the chamfers 200 elongate the loading zone to increase the area over which the load is transferred between the support member 140 including the stem portion 150, keels 170, pegs 180, and bridges 190 and the tray 120. In use, the chamfer or loading zones 200 act to provide a variable thickness to guide transfer of the load between the support member 140 including the stem portion 150, keels 170, pegs 180, and bridges 190 and the tray 120. That is, the chamfer or loading zones 200 act to increase the thickness of the tibial tray 120 adjacent to the support member 140 including the stem portion 150, keels 170, pegs 180, and bridges 190. At the same time, the chamfer or loading zones 200 facilitate maintaining a constant overall combined thickness of the tibial component (e.g., combined thickness of the tibial tray 120 and the porous layer 110). That is, the chamfer or loading zones 200 enable the thickness of the tray 120 to be increased while the overall combined thickness of the tibial component remains constant across the surface area of the tibial component (e.g., during application of the porous layer 110, the thickness of the porous layer 110 can be minimized over the chamfer or loading zones 200 so that the overall combined thickness of the tibial component (e.g., combined thickness of the tray and the porous layer) remains constant).

In use, the chamfer or loading zones 200 may have any size and shape arranged and configured to facilitate transfer of the load between the support member 140 including the stem portion 150, keels 170, pegs 180, and bridges 190 and the tray 120. As illustrated, in one embodiment, the chamfer or loading zone 200 may have a substantially circular shape extending from and about the support member 140 including the stem portion 150, keels 170, pegs 180, and bridges 190. As shown, in one embodiment, adjacent chamfers 200 may blend, overlap with, etc. each other. In use, the chamfer or loading zones 200 transition from a first height adjacent to the radiused surface 210 to a second height extending away from the support member 140 including the stem portion 150, keels 170, pegs 180, and bridges 190, the first height being larger than the second height. In one embodiment, the height of the chamfer or loading zones 200 may extend or taper from approximately 0 to approximately 10 mm, preferably in one embodiment, the height of the chamfer or loading zones 200 may extend from approximately 0 to approximately 1,000 μm. Additionally, in one embodiment, the chamfer or loading zones 200 may extend or taper outwardly over a length of approximately 0 to approximately 20 mm plus, preferably in one embodiment the chamfer or loading zones 200 may extend or taper outwardly over a length of approximately 0 to approximately 8,000 μm (e.g., the outward extent of the chamfer or loading zones 200 only being limited by the overall size of the implant).

Figure 5:
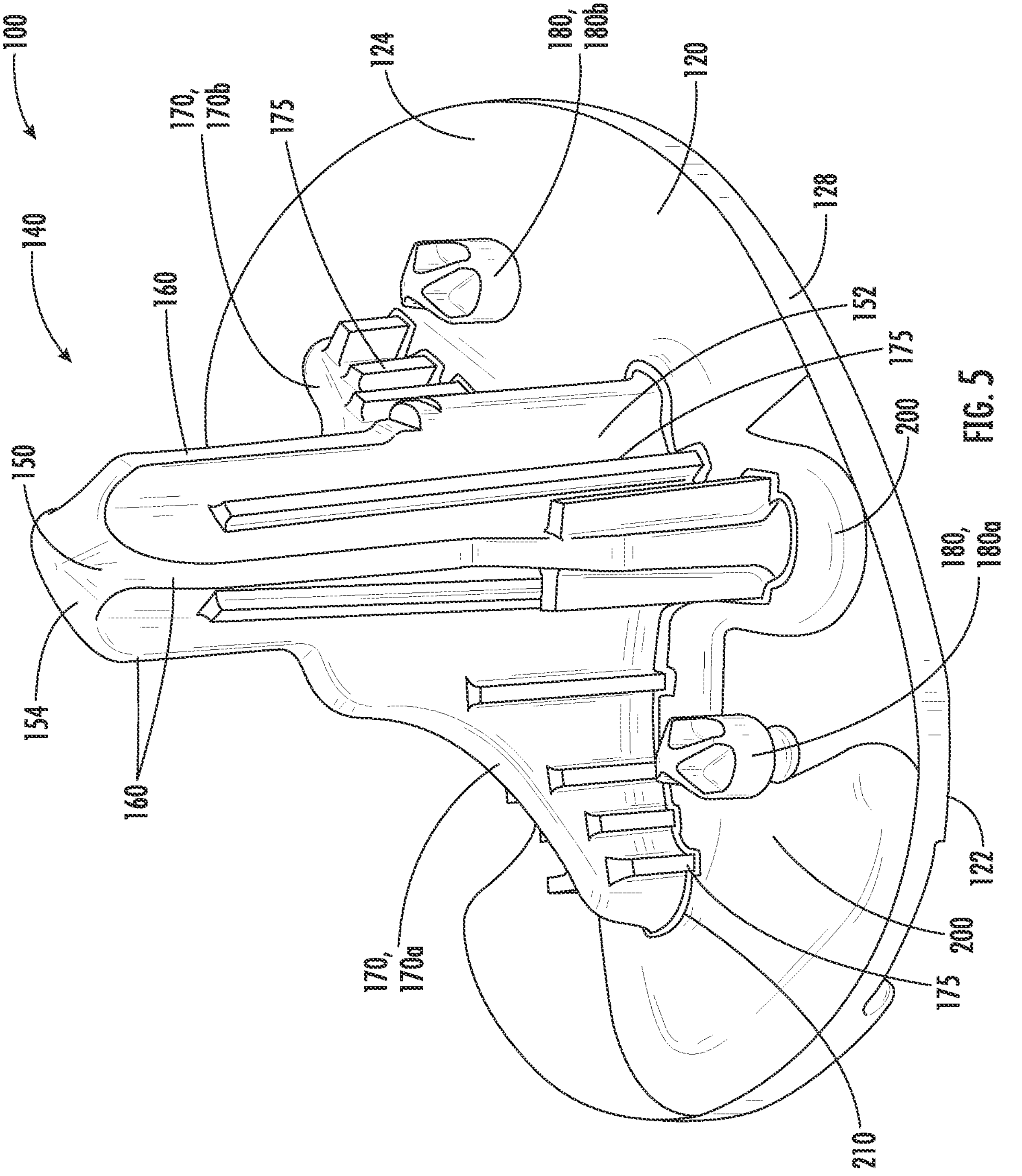
FIG. 5 is a bottom, perspective view of an alternate example of an embodiment of a tibial implant in accordance with one or more features of the present disclosure, the tibial implant shown with the porous layer removed.

Alternatively, referring to FIG. 5, in an alternate example of an embodiment, the chamfer or loading zone 200 can be blended into (e.g., combined) with the radiused surface 210 transitioning between the support member 140 including the stem portion 150, keels 170, pegs 180, and bridges 190 and the bottom surface 124 of the tray 120. Thus arranged, the loading zone 200 includes an increased thickness that is blended in with the radii.

Figure 6:
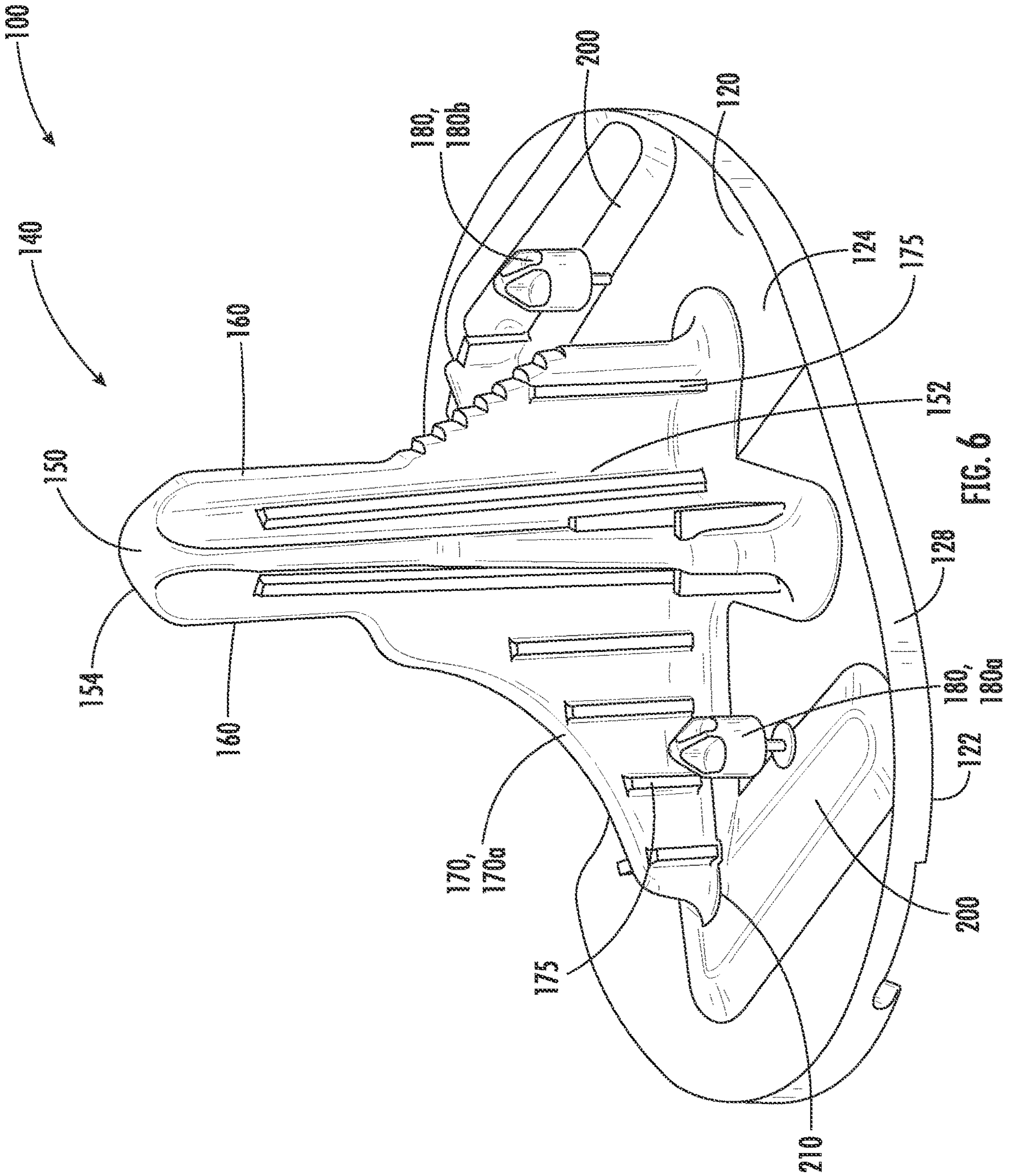
FIG. 6 is a bottom, perspective view of an alternate example of an embodiment of a tibial implant in accordance with one or more features of the present disclosure, the tibial implant shown with the porous layer removed.

Alternatively, referring to FIG. 6, in an alternate example of an embodiment, the bridge 190 and the chamfer/loading zone 200 may be blended together to create a reduced profile transition between the pegs 180 and the support member 140 (e.g., keels 170). In this manner, the bridge 190 is substantially hidden from view when the porous layer is applied.

Figure 7:
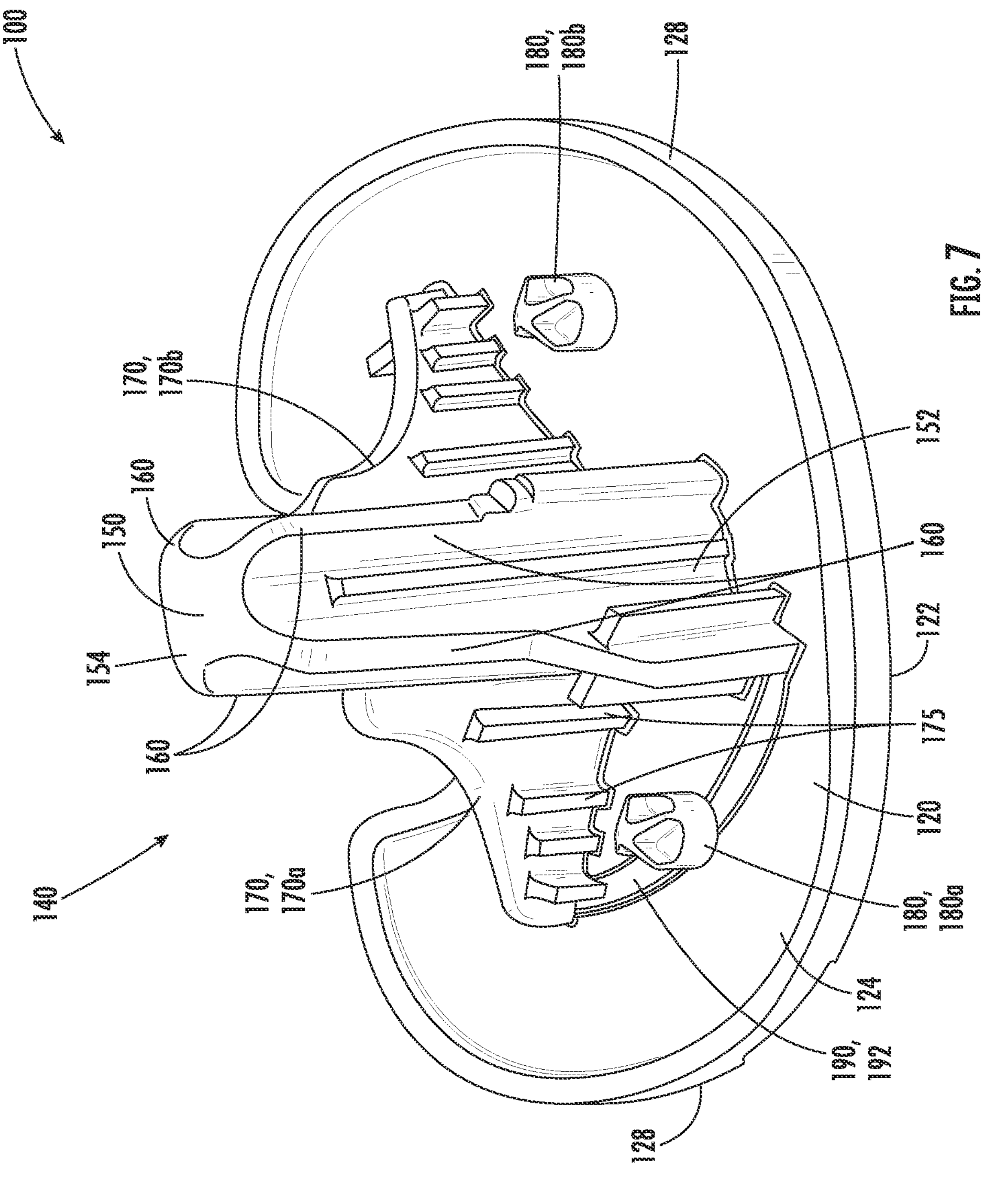
FIG. 7 is a bottom, perspective view of an alternate example of an embodiment of a tibial implant in accordance with one or more features of the present disclosure, the tibial implant shown with the porous layer removed.

Alternatively, referring to FIG. 7, in an alternate example of an embodiment, the bridge 190 may be provided in the form of a rail 192 between and coupling adjacent keels 170. That is, as illustrated, the pegs 180 may be positioned on the rail 190, which extends between adjacent keels 170.

Referring to FIGS. 9-13, an alternate example of an embodiment of a tibial implant 100 is illustrated. In use, the tibial implant 100 is substantially similar to the previous embodiments described herein. As such, for the sake of brevity, discussion of some components is omitted herefrom.

Figure 13:
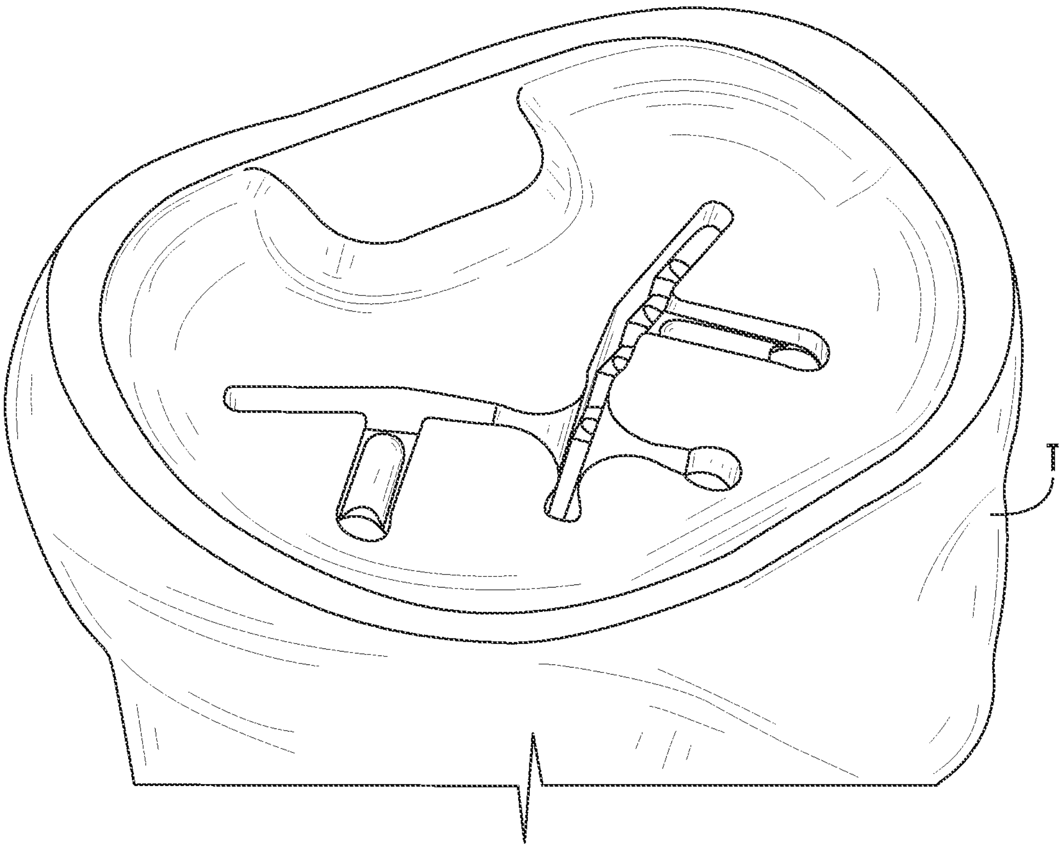
FIG. 13 illustrates a perspective view of an example of an embodiment of a prepared tibial, the prepared tibial being arranged and configured to receive the tibial implant shown in FIG. 9.

FIGS. 9-12 illustrate various views of the tibial implant 100. FIG. 13 illustrates a perspective view of a patient's tibial, the patient's tibial being prepared to receive the tibial implant 100 shown in FIGS. 9-12. Referring to FIGS. 9-12, the tibial implant 100 is illustrated with the porous layer 110 coupled thereto or mounted thereon.

Similar to the embodiments previously described herein, the tibial implant 100 includes a tibial tray 120 connected to a support member 140. In addition, the tibial tray includes a top or superior surface 122 and a bottom or inferior surface 124. As previously mentioned, and as illustrated, the bottom surface 124 of the tibial tray 120 includes a porous layer or coating 110 applied thereto.

Similar to the embodiments previously described herein, the support member 140 extends from the bottom surface 124 of the tibial tray 120. In use, the support member 140 is positioned, at least partially, within the intramedullary canal of the patient's tibia T (FIG. 13) to couple the tibial implant 100 to the patient's tibia T. The support member 140 includes a stem portion 150 that extends away from the bottom surface 124 of the tibial tray 120 along a longitudinal axis L. The longitudinal axis L may be substantially perpendicular to the bottom surface 124 of the tibial tray 120 in the medial-lateral direction. The stem portion 150 may be positioned offset from a center of the tibial tray 120 (e.g., positioned more medial than lateral). For example, in one embodiment, the stem portion 150 may be medialized slightly from the center of the tibial tray 120. The tibial tray 120 may include a slope in the anterior-posterior direction. In some embodiments, the stem portion 150 may include a first portion 152 adjacent to the bottom surface 124 of the tibial tray 120 and a second portion 154 that extends away from the first portion 152. The first portion 152 may have a first cross sectional area and the second portion 154 may have a second cross sectional area wherein the first cross sectional area is larger than the second cross sectional area. In other embodiments, the second portion 154 can have the same cross sectional area and shape as the first portion 152. In use, the stem portion 150 has a length that is sized to promote varus-valgus stability and resistance of the tibial tray 120 to liftoff from the patient's bone.

In addition, in one embodiment, as previously mentioned and as shown, the support member 140 may include one or more fins 160 spaced about the stem portion 150. In use, the fins 160 assist in providing rotational stability and help with implantation and alignment of the tibial tray 120 in bone upon implantation. Any or all of the fins 160 can also be sized to a maximum that is implantable based on the anatomy of the patient.

In addition, as previously mentioned and as shown, the support member 140 may also include one or more posterior keels 170. As shown, the support member 140 may include first and second posterior keels 170*a*, 170*b* mounted on the bottom surface 124 of the tibial tray 120 extending from either side of the stem portion 150 posteriorly towards the posterior side P of the tibial tray 120, although this is just one configuration and more or less keels 170 and/or different configurations of keels 170 may be utilized. In use, the keels 170 may increase the strength of the implant 100 while also helping to prevent rotation of the tibial implant 100 relative to the patient's bone (e.g., keels 170 assist with rotational stability of the tibial tray 120 in bone upon implantation).

In use, and as previously described, the first and second keels 170*a*, 170*b*, as well as other components of the support member 140, may include a plurality of ridges 175 that extend along the height or a portion of the keels 170 as measured along the longitudinal axis L. In one embodiment, the plurality of ridges 175 may have a square or semi square cross sectional shape however in other forms the shape may be rectangular or semicircular. In use, the plurality of ridges 175 assist with added bone compression and fixation strength of the tibial implant 100 in the patient's bone.

Beneficially, the fins 160 and the keels 170 provide increased rotational resistance and strength for the tibial implant 100 when implanted. The configuration of the support member 140 including the stem portion 150, fins, 160, and keels 170 provide improved fixation between the tibial tray 120 and the patient's bone post-operatively. Moreover, the fins 160 positioned on the anterior side A of the tibial tray 120 are more sensitive to anatomic dimensions of the patient's bone than the fins 160 positioned on the posterior side P therefore the size, location, and position of the anterior fins 160 on the tibial tray 1120 are more sensitive than the posterior fins 160.

In addition, as illustrated, in one example of an embodiment, the tibial tray 120 may also include one or more pegs 180. For example, as shown, the tibial implant 100 may include first and second pegs 180*a*, 180*b*, although this is but one configuration and more or less pegs may be used. As illustrated, the first and second pegs 180*a*, 180*b* may be mounted on the bottom surface 124 of the tibial tray 120. In one embodiment, as illustrated, the first and second pegs 180*a*, 180*b* may be positioned closer to the rim or periphery edge 128 of the tibial tray 120. The first and second pegs 180*a*, 180*b* approach the tibial plateau for added stability of the tibial tray 120, and enter into denser bone than in the central canal upon implantation. Additional pegs 180 can be mounted as desired. The pegs 180 can have any suitable size and shape arranged and configured to engage the patient's bone to provide increased stability. For example, as shown, the pegs 180 may be substantially cylindrical with a pointed tip, although other shapes are envisioned such as, for example, an arrowhead shape.

As previously mentioned, and illustrated, in accordance with one or more features of the present disclosure, in use, the pegs 180 such as, for example, the first and second pegs 180*a*, 180*b* may be coupled to the support member 140 such as, for example, to the first and second keels 170*a*, 170*b*, respectively, via a bridge 190 (FIGS. 1-4). In use, the bridge 190 is arranged and configured to couple the first and second pegs 180*a*, 180*b* to the first and second keels 170*a*, 170*b*, respectively, so that any loads received by the first and second pegs 180*a*, 180*b* can be transferred to the support member 140 via the first and second keels 170*a*, 170*b*. Thus arranged, any anterior load can be carried back from the pegs 180, which are positioned anteriorly on the tray 120 to capture the anterior loads, to the keels 170 and subsequently to the support member 140 thereby providing the tibial tray 120 with increased strength to avoid breakage due to an associated anterior loading condition. That is, in contrast with known implants, by coupling the pegs 180 to the support member 140 via, for example, the keels 170, the anterior load is transferred from the pegs 180 to the keels 170 and to the stem portion 150 of the support member 140 instead of to the tray 120 thereby providing increased strength to avoid damage such as breakage of the tray.

In addition, and as previously mentioned, in accordance with one or more features of the present disclosure that may be used in combination with the pegs 180 and bridges 190 disclosed above or separately therefrom, the tibial tray 120 may include one or more chamfers 200 (FIGS. 3 and 4) formed in the bottom or inferior surface 124 thereof. In addition, the support member 140 including the stem portion 150, keels 170, pegs 180, and bridges 190 may include a radiused surface 210 at the connection or formation to the bottom surface 124 of the tibial tray 120. In use, the radiused surface 210 facilitates transferring load between the support member 140 including the stem portion 150, keels 170, pegs 180, and bridges 190 and the tray 120 by preventing, or at least minimizing stress concentrations (e.g., the radiused surfaces 210 help to facilitate better load transfer back towards the support member). The one or more chamfers 200 may be formed between the radiused surface 210 and the bottom surface 124 of the tibial tray 120.

In use, the chamfer or loading zones 200 act to provide a variable thickness to guide transfer of the load between the support member 140 including the stem portion 150, keels 170, pegs 180, and bridges 190 and the tray 120. That is, the chamfer or loading zones 200 act to increase the thickness of the tibial tray 120 adjacent to the support member 140 including the stem portion 150, keels 170, pegs 180, and bridges 190.

Referring to FIGS. 9-13, in accordance with one or more features of the present disclosure, the porous coating 110 may be include a non-faceted bottom surface 220 (e.g., a non-planar surface). In one embodiment, as illustrated, the porous coating 110 may include a planar surface along an interior region or area of the tibial tray 120 adjacent to the support member 140, the non-faceted bottom surface 220 may be provided adjacent to the periphery surface 128 of the tibial tray 120.

In use, the non-faceted bottom surface 220 of the porous coating 110 may be arranged and configured to conceal, for example, one or more bridges 190, chamfers or loading zones 200, and/or radiused surfaces 210. In addition, the non-faceted bottom surface 220 of the porous coating 110 may be arranged and configured to provide the tibial tray 120 with an increased thickness adjacent to the support member 140. In one embodiment, the non-faceted bottom surface may commence a distance from the periphery surface 128 of the tibial tray 120 and may provide a radiused or transitioned area or surface 225 arranged and configured along a periphery of the non-faceted bottom surface 220, the radiused or transitioned area or surface 225 arranged and configured to transition from the non-faceted bottom surface 220 to the tibial tray 120. Thus arranged, the tibial tray 120 includes an area of increased thickness (e.g., non-faceted bottom surface 220) that is blended in with the trial tray 120 via a radiused or transitioned area or surface 225 (e.g., a radiused transition is provided between the non-faceted bottom surface 220 and the tibial tray 120) to guide distribution of a load between the support member 140 and the tibial tray 120.

In use, as illustrated in FIG. 13, the non-faceted bottom surface 220 of the tibial tray 110 is arranged and configured to be positioned within or nest into a precision prepared proximal tibia T of the patient. In use, the patient's proximal tibia T may be prepared using precision milling via, for example, a bur associated with a robotic surgical system, although any other mechanisms for preparing the patient's proximal tibial T may be used.

As previously mentioned herein, the tibial implant can be manufactured from any suitable bio-compatible material now known or hereafter developed used to manufacture orthopedic implants including, for example, titanium, cobalt chrome, stainless steel, ceramic or other biocompatible material. In addition, and/or alternatively, the tibial implant may be formed using any desired or appropriate methodologies or technologies now known or hereafter developed. For example, in one embodiment, the tibial implant may be manufactured using any now known or hereafter developed additive manufacturing technique. By way of some, non-limiting known techniques, the tibial implant could be manufactured from selective laser sintering (SLS), direct metal laser sintering (DMLS), electron beam melting (EBM), selective laser melting (SLM), three-dimensional printing, or the like. For instance, in some embodiments, the entire tibial implant may be formed as a monolithic or integral implant (including any porous or other in-growth promoting surfaces or materials). In some embodiments, portions of the tibial implant may be formed and then additional in-growth materials, surfaces, and/or treatments could be added or applied to the implant. In other embodiments, an additive manufacturing technique such as, for example, electron beam melting methods or methods that use lasers to subtract or remove select portions of material from an initially solid material may be used. In other embodiments, portions or all of the tibial implant can be formed using casting or other technologies or methods. In some embodiments, a non-porous implant such as a tibial implant may be formed using an additive manufacturing technique such as, for example, SLS technologies and subsequently that implant may be subjected to acid etching, grit blasting, plasma spraying (e.g. of titanium oxide or another metal to promote in-growth) or other treatments.

In use, the tibial implant may be part of a set of tibial implants of various standard sizes, or may be a patient-matched tibial implant with certain geometries and/or other features of the implant customized for a particular patient's anatomy.

Terms such as top, bottom, superior, inferior, medial, lateral, anterior, posterior, proximal, distal, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments. Rather these embodiments should be considered as illustrative and not restrictive in character. All changes and modifications that come within the spirit of the invention are to be considered within the scope of the disclosure. The present disclosure should be given the full scope defined by the language of the following claims, and equivalents thereof.

The foregoing description has broad application. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However, such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

As used herein, an element or step recited in the singular and proceeded with the word "a" or "an" should be understood as not excluding plural elements or steps, unless such exclusion is explicitly recited.

The phrases "at least one", "one or more", and "and/or", as used herein, are open-ended expressions that are both conjunctive and disjunctive in operation. The terms "a" (or "an"), "one or more" and "at least one" can be used interchangeably herein. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments or configurations. Moreover, the following claims are hereby incorporated into this Detailed Description by this reference, with each claim standing on its own as a separate embodiment of the present disclosure.

The invention claimed is:

1. A tibial implant comprising:

a tibial tray including a top surface and a bottom surface; and a support member extending from the bottom surface of the tibial tray, the support member being arranged and configured to be at least partially positioned within an intramedullary canal of a patient's bone for coupling the tibial implant to the patient's bone during use, the support member including:

a stem portion; and one or more keels extending from the stem portion;

wherein the tibial implant further comprises a chamfer loading zone between the bottom surface of the tibial tray and the support member, the chamfer loading zone providing a variable thickness transition area between the bottom surface of the tibial tray and the support member to transfer loads between the tibial tray and the support member;

wherein the bottom surface of the tibial tray further comprises a porous layer mounted thereon, at least a portion of the porous layer comprises a non-faceted bottom surface arranged and configured to provide a variable thickness transition area between the bottom surface of the tibial tray and the support member to guide distribution of a load between the tibial tray and the support member.

2. The tibial implant according to claim 1, wherein the chamfer loading zone is positioned between a radiused surface associated with the support member and the bottom surface of the tibial tray.

3. The tibial implant according to claim 1, wherein each of the stem portion and the one or more keels includes a chamfer loading zone extending therefrom.

4. The tibial implant according to claim 3, wherein each of the chamfer loading zones includes a circular shape extending outwardly from the support member.

5. The tibial implant according to claim 1, wherein the support member further comprises one or more pegs positioned anteriorly on the bottom surface of the tibial tray and one or more bridge members coupling the one or more pegs to the one or more keels, respectively, the one or more bridge members arranged and configured to transfer loads from the one or more pegs to the one or more keels.

6. The tibial implant according to claim 5, wherein the one or more keels includes first and second keels, the one or more pegs include first and second pegs, and the one or more bridge members include first and second bridge members, the first peg being coupled to the first keel via the first bridge member, the second peg being coupled to the second keel via the second bridge member.

7. The tibial implant according to claim 6, wherein the first keel extends from the medial side of the stem portion toward the medial side of the tibial tray, the second keel extends from the lateral side of the stem portion toward the lateral side of the tibial tray.

8. The tibial implant according to claim 7, wherein the first and second keels extend posteriorly from the stem portion.

9. The tibial implant according to claim 6, wherein the first and second pegs are positioned closer to a periphery edge of the tibial tray as compared to the stem portion, and the first and second pegs are positioned anteriorly as compared to the stem portion.

10. The tibial implant according to claim 1, wherein the support member includes one or more protrusions coupled to the stem portion, the one or more protrusions extending along a longitudinal length of the stem portion.

11. The tibial implant according to any claim 10, wherein the support member further includes one or more protrusions coupled to the one or more keels, the one or more protrusions extending along a longitudinal length of the keels.

12. The tibial implant according to claim 1, wherein the tibial tray and the support member including the stem portion and the one or more keels are monolithically or integrally formed.

13. A tibial implant comprising:

a tibial tray including a top surface and a bottom surface; and a support member extending from the bottom surface of the tibial tray, the support member being arranged and configured to be at least partially positioned within an intramedullary canal of a patient's bone for coupling the tibial implant to the patient's bone during use, the support member including a stem portion and one or more keels extending from the stem portion;

wherein the bottom surface of the tibial tray further comprises a porous layer mounted thereon, at least a portion of the porous layer comprises a non-faceted bottom surface arranged and configured to provide a variable thickness transition area between the bottom surface of the tibial tray and the support member to guide distribution of a load between the tibial tray and the support member.

14. The tibial implant according to claim 13, wherein the support member further comprises one or more pegs positioned anteriorly on the bottom surface of the tibial tray and one or more bridge members coupling the one or more pegs to the one or more keels, respectively, the one or more bridge members arranged and configured to transfer loads from the one or more pegs to the one or more keels.

15. The tibial implant according to claim 14, wherein the one or more keels includes first and second keels, the one or more pegs include first and second pegs, and the one or more bridge members include first and second bridge members, the first peg being coupled to the first keel via the first bridge member, the second peg being coupled to the second keel via the second bridge member.

16. The tibial implant according to claim 15, wherein the first keel extends from the medial side of the stem portion toward the medial side of the tibial tray, the second keel extends from the lateral side of the stem portion toward the lateral side of the tibial tray.

17. The tibial implant according to claim 16, wherein the first and second keels extend posteriorly from the stem portion.

18. The tibial implant according to claim 15, wherein the first and second pegs are positioned closer to a periphery edge of the tibial tray as compared to the stem portion, and the first and second pegs are positioned anteriorly as compared to the stem portion.

19. The tibial implant according to claim 13, wherein the tibial tray and the support member including the stem portion and the one or more keels are monolithically or integrally formed.

* * * * *